United States Patent
Zarczuk

(10) Patent No.: US 12,263,119 B2
(45) Date of Patent: Apr. 1, 2025

(54) OPTHALMIC DISPENSING DEVICE

(71) Applicant: Zaklady Farmaceutyczne Polpharma S.A., Starogard Gdanski (PL)

(72) Inventor: Jakub Zarczuk, Karolkowa (PL)

(73) Assignee: Zaklady Farmaceutyczne Polpharma S.A., Starogard Gdanski (PL)

( * ) Notice: Subject to any disclaimer, the term of this patent is extended or adjusted under 35 U.S.C. 154(b) by 996 days.

(21) Appl. No.: 17/259,017

(22) PCT Filed: Jul. 9, 2019

(86) PCT No.: PCT/PL2019/000052
§ 371 (c)(1),
(2) Date: Jan. 8, 2021

(87) PCT Pub. No.: WO2020/013717
PCT Pub. Date: Jan. 16, 2020

(65) Prior Publication Data
US 2021/0282965 A1    Sep. 16, 2021

(30) Foreign Application Priority Data
Jul. 9, 2018 (EP) .................... 18460042

(51) Int. Cl.
*A61F 9/00* (2006.01)
*A61K 9/00* (2006.01)
*A61K 31/5377* (2006.01)
*A61K 31/5575* (2006.01)
*A61K 47/02* (2006.01)
*A61K 47/26* (2006.01)

(52) U.S. Cl.
CPC .......... *A61F 9/0008* (2013.01); *A61K 9/0048* (2013.01); *A61K 31/5377* (2013.01); *A61K 31/5575* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | | | |
|---|---|---|---|---|
| 2,877,810 A | * | 3/1959 | Zackheim | B01L 3/0282 422/934 |
| 2001/0002012 A1 | * | 5/2001 | Yeaton | B65D 41/0442 215/44 |
| 2005/0287325 A1 | | 12/2005 | Baket et al. | |
| 2007/0297990 A1 | * | 12/2007 | Shah | A61K 33/26 514/217.05 |
| 2010/0216877 A1 | * | 8/2010 | Kshirsagar | A61P 27/02 514/622 |
| 2016/0082194 A1 | * | 3/2016 | Furukawa | A61M 5/31513 604/222 |

FOREIGN PATENT DOCUMENTS

| | | | | |
|---|---|---|---|---|
| EP | 2193795 | | 6/2010 | |
| WO | WO 2009/145356 | | 12/2009 | |
| WO | WO-2017182138 A1 | * | 10/2017 | ......... A61K 31/5377 |

OTHER PUBLICATIONS

International Search Report for PCT/PL2019/000052, issued Oct. 28, 2019.

* cited by examiner

*Primary Examiner* — Melissa S Mercier
(74) *Attorney, Agent, or Firm* — King & Spalding LLP

(57) ABSTRACT

The present invention is directed to a dispensing device comprising: an ophthalmic liquid composition comprising a prostaglandin analogue; a container with the ophthalmic liquid composition comprising a prostaglandin analogue packaged therein; a dropper; and a gasket, wherein the gasket is made of a polymer substantially free of ethylene-vinyl acetate or plasticiser. The present invention further refers to a dropper and a gasket for the dispensing device and to a preservative-free aqueous ophthalmic composition of latanoprost.

19 Claims, No Drawings

OPTHALMIC DISPENSING DEVICE

CROSS REFERENCE TO RELATED APPLICATIONS

This application is a national phase application under 35 U.S.C. § 371 of International Application No. PCT/PL2019/000052, filed Jul. 9, 2019, which claims priority to European Patent Application No. 18460042.7, filed Jul. 9, 2018. The contents of each of the above-identified applications is hereby fully incorporated herein by reference.

TECHNICAL FIELD

The present invention relates to a dispensing device comprising an ophthalmic liquid composition comprising a prostaglandin analogue.

BACKGROUND ART

Prostaglandins or prostaglandin analogues are well-known active ingredients, generally administered to humans or animals topically in the form of eye drops for the treatment of glaucoma, and a number of prostaglandin analogues have been studied and developed.

However, some prostaglandins analogues are hardly soluble in water and liable to be adsorbed to any part of the dispenser that is in contact with the solution. This phenomena is particularly critical at low concentrations because the delivery of the required amount of the active ingredient over time cannot be ensured.

Indeed, if the active ingredient reacts, reversibly or not, with one of the component materials of the device when in contact, its concentration in the solution decreases and may become too low to have an optimal therapeutic effect.

One way to solve this problem is to modify the formulation of the solution in order to make the solution stable and inert with respect to the material of the storage and dispensing device, even at low concentrations.

Currently there are many types of dispensing devices available on the market containing droppers having various parts, such as a valve support, a dispensing valve, air take-up member, filter element, filter element holder, etc. These parts can be made of different materials and therefore it is difficult to adapt the formulation of the solution to all the materials of the device in contact with the solution.

For liquid preparations containing the prostaglandin analogues revealing such inconveniencies mentioned above, it is necessary to improve the matters of adsorption on a dispenser and solubility in water.

In the prior art some proposals to solve the problem of adsorption of prostaglandin analogues are known.

WO2002/22106 A1 discloses that prostaglandin can be stably stored in a resin container comprising polypropylene.

WO2005/011704 A1 discloses that prostaglandin can be stably stored in a resin container formed from a polymer alloy of polyethylene terephthalate and polyarylate.

WO2010/100656 provides a stable method for storing a pharmaceutical composition comprising prostaglandin(s) wherein the method comprises the step of storing the prostaglandin composition in polyethylene container, preferably low density polyethylene (LOPE), still preferably LDPE container having Purell PE 3020 D resin, which container is made using Blow Fill Seal (BFS) technology.

WO2013/038120 is related to a device for the storage and dispensing of pharmaceutical liquid comprising, on at least a part of an internal surface of the device, a coating reducing the adsorption of at least one of the species present in the liquid.

However, not only the container but other parts of the dispensing device that are also in contact with the liquid composition have not been studied.

WO2002/022131 discloses an invention wherein solubility in water and adsorption on a resin container of a prostaglandin analogue are improved by incorporating a non-ionic surfactant and/or an antioxidant in an ophthalmic solution.

WO2009/145356 is related to preservative-free ophthalmic composition containing PGF2alpha analogues, non-ionic surfactant, stabilizing agent in a container consisting essentially of polyethylene. Specific excipients are required in order to stabilize the solution.

Therefore it exists a need in the art for a device for storing and dispensing ophthalmic liquid compositions comprising a prostaglandin analogue that makes it possible to guarantee the active ingredient content in the solution for a given time interval, without having to adapt the composition of the solution to the different materials of the device.

DISCLOSURE OF THE INVENTION

The present inventor noticed that for a dispensing device which comprises a container, a dropper and a gasket placed between the dropper and the container, the above mentioned means to eliminate adsorption of prostaglandin analogues are not effective. Adsorption of the above active substances negatively affects its content despite of presence of surfactants and materials of a container, as disclosed in the prior art.

The problem to be solved by the present invention is to provide a dispensing device comprising a container with an ophthalmic liquid composition comprising a prostaglandin analogue packaged therein, a dropper and a gasket, which prevents the concentration of the prostaglandin analogue in the liquid composition from decreasing.

Dispensing devices currently available on the market comprise gasket having plasticizer, such as ethylene-vinyl acetate (Evatane®).

A first aspect of the present invention relates to a dispensing device comprising a container with an ophthalmic liquid composition comprising a prostaglandin analogue packaged therein, a dropper and a gasket, wherein said gasket is made of a polymer substantially free of ethylene-vinyl acetate.

Another aspect of the present invention refers to a dispensing device comprising a container with an ophthalmic liquid composition comprising a prostaglandin analogue packaged therein, a dropper and a gasket, wherein said gasket is made of a polymer substantially free of plasticiser.

Yet further aspect of the present invention refers to a gasket for the dispensing device according to any of the previous aspects, wherein said gasket is made of a polymer substantially free of ethylene-vinyl acetate.

The next aspect of the present invention refers to a gasket for the dispensing device according to any of the previous aspects, wherein said gasket is made of a polymer substantially free of plasticiser.

A further aspect of the present invention refers to a dropper for the dispensing device according to any of the previous aspects, comprising a gasket made of a polymer substantially free of ethylene-vinyl acetate.

Still further aspect of the present invention refers to a dropper for the dispensing device according to any of the previous aspects, comprising a gasket made of a polymer substantially free of plasticiser.

Another aspect of the present invention refers to a dispensing device for an ophthalmic liquid composition comprising a prostaglandin analogue, comprising;
  a container for the ophthalmic liquid composition;
  a dropper; and
  a gasket
  wherein the gasket is made of a polymer substantially free of ethylene-vinyl acetate.

Another aspect of the present invention refers to a dispensing device for an ophthalmic liquid composition comprising a prostaglandin analogue, comprising;
  a container for the ophthalmic liquid composition;
  a dropper; and
  a gasket
  wherein the gasket is made of a polymer substantially free of plasticiser.

Another aspect of the present invention refers to a dispensing device comprising a container with a preservative-free ophthalmic aqueous solution comprising a prostaglandin analogue packaged therein, a dropper and a gasket, said gasket is made of a polymer substantially free of ethylene-vinyl acetate.

Another aspect of the present invention refers to a preservative-free aqueous ophthalmic solution comprising latanoprost, optionally in combination with timolol or a pharmaceutically acceptable salt thereof, polysorbate 80, disodium edetate, a tonicity agent, a buffering agent, optionally a pH adjusting agent, and water as solvent.

A dispensing device is to be understood as a drug delivery system for storing and dispensing a therapeutic solution and is referred herein also as a device or dispenser.

A dropper as referred herein should be also understood as a closure system, which is suitable for ejecting or dispensing individual drops of a liquid.

A gasket which is also named a sealing ring disk, is arranged between the container and the dropper by sealing the connection. The gasket can be either inserted in the dropper or fixed at the top of the neck of the container.

As used herein, the term "ophthalmic liquid composition" refers to various dosage forms suitable for topical ophthalmic delivery or eye drops, including solutions, suspensions, emulsions, powders for reconstitution, gels and erodible solid ocular inserts. In a specific embodiment the term "ophthalmic liquid composition" refers to a solution.

As used herein, the phrase "a gasket substantially free of" refers to a gasket made of a polymer that includes none of ethylene-vinyl acetate or plasticiser, or that includes less than 5%, preferably less than 4%, more preferably less than 3%, more preferably less than 2%, more preferably less than 1% and even more preferably 0% of ethylene-vinyl acetate or plasticiser.

As used herein, the phrase "a gasket substantially free of" refers to a gasket made of a polymer that includes none of ethylene-vinyl acetate or plastisicer or that it is at such a low concentration as not to exert its adsorption effect.

The present inventors have surprisingly found that the stability in terms of undesired adsorption of an active substance of an ophthalmic liquid composition comprising a prostaglandin analogue in a dispensing device with a gasket made of a polymer substantially free of ethylene-vinyl acetate or plasticiser, surprisingly increased when compared to the same composition in the devices with a gasket made of polymer with plasticiser.

The present inventors have further found that the prostaglandin adsorption in the dispensing device can be prevented to significant level. Assay testing confirmed that the prostaglandin product stored in the inventive dispensing device provided with a gasket substantially free of plasticiser or ethylene-vinyl acetate meets requirements of the specification both at release and at the end of shelf life (e.g. assay by HPLC is within 95-105% at release and 90-105% at the end of shelf life). Additional laboratory testing confirmed that lack of the plasticizer or ethylene-vinyl acetate in the gasket surprisingly does not adversely affect the tightness of the packaging.

Along the present description, as well as in the claims, the singular expressions, generally preceded by the articles "a", "an" or "the", are meant to include also the plural forms, unless the context clearly indicates otherwise. Furthermore, numeric values preceded by the term "about" are meant to include the exact stated value and also a certain variation around such value, namely a variation or ±5% of the stated amount. Numeric ranges defined by lower and upper endpoints are meant to include also said stated endpoints.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

The invention refers to a dispensing device comprising a container with an ophthalmic liquid composition comprising a prostaglandin analogue packaged therein, a dropper and a gasket made of a polymer substantially free of ethylene-vinyl acetate.

Further, the invention refers to a dispensing device comprising a container with an ophthalmic liquid composition comprising a prostaglandin analogue packaged therein, a dropper and a gasket made of a polymer substantially free of plasticiser.

Part of the invention is also a gasket for the dispensing device according to any of the previous aspects, wherein it is made of a polymer substantially free of ethylene-vinyl acetate.

Further, invention concerns a gasket for the dispensing device according to any of the previous aspects, wherein it is made of a polymer substantially free of plasticiser.

The invention also refers to a dropper for the dispensing device according to the invention, comprising a gasket made of a polymer substantially free of ethylene-vinyl acetate.

And it refers to a dropper for the dispensing device according to any of the previous aspects, comprising a gasket made of a polymer substantially free of plasticiser.

The invention also refers to a preservative-free aqueous ophthalmic solution comprising latanoprost, optionally in combination with timolol or a pharmaceutically acceptable salt thereof, polysorbate 80, disodium edetate, a tonicity agent, a buffering agent, optionally a pH adjusting agent, and water as solvent.

As is shown in the comparative stability tests 1, 2, 5 and 6 (tables 1, 2, 5 and 6), surprisingly, the ophthalmic liquid compositions assayed, comprising a prostaglandin analogue (latanoprost, travoprost or tafluprost) were more stable when they were stored in a dispensing device comprising a gasket which was made of a polymer substantially free of ethylene-vinyl acetate or any other plasticiser, compared to equivalent formulations stored in dispensing devices with a gasket made of PE/EVA which comprises ethylene-vinyl acetate (EVA).

In a first embodiment of the present invention, optionally in combination with one or more features of the various embodiments described above or below, the dispensing device comprises an ophthalmic liquid composition comprising a prostaglandin analogue packaged in a container, wherein the prostaglandin analogue is a prostaglandin F2α analogue. In a preferred embodiment, the prostaglandin F2α analogue is selected from esters of prostaglandin F2α analogues. In a more preferred embodiment, an ester of prostaglandin F2α analogue is selected from the group consisting of latanoprost, travoprost and tafluprost.

The adsorption phenomena is particularly critical with esters of prostaglandin F2α analogues.

In another embodiment of the present invention, optionally in combination with one or more features of the various embodiments described above or below, the dispensing device as disclosed herein, comprises the ophthalmic liquid composition comprises a prostaglandin analogue in a concentration up to 100 micrograms/millilitre.

The adsorption phenomena is particularly critical at low concentrations (e.g. up to 100 micrograms/millilitre of active ingredient) because the delivery of the required amount of the active ingredient over time it not ensured and an optimal therapeutic effect may not be provided.

In a preferred embodiment of the present invention, optionally in combination with one or more features of the various embodiments described above or below, the dispensing device is provided, wherein the ophthalmic liquid composition is preferably an aqueous solution, an emulsion or a suspension, and more preferably is an aqueous solution.

The most commonly employed ophthalmic dosage forms are solutions.

The ophthalmic liquid composition according to the invention may also comprise conventional excipients used in ophthalmic compositions, such as surfactants, antioxidants, tonicity agents, buffering agents and the like.

The term "surfactant" refers to a compound that lowers the surface tension between two liquids or between a liquid and a solid. Materials commonly used as surfactants include: (a) non-ionic surfactants such as polyoxyethylene fatty alcohol ethers, sorbitan fatty acid esters, polyoxyethylene fatty acid esters, sorbitan esters, glycerol monostearate, polyethylene glycols, acetyl alcohol, cetostearyl alcohol, stearyl alcohol and poloxamers; (b) anionic surfactants such as potassium laurate, triethanolamine stearate, sodium lauryl sulfate and alkyl polyoxyethylene sulfates; and (c) cationic surfactants such as chitosans; and mixtures thereof.

In one embodiment of the present invention, optionally in combination with one or more features of the various embodiments described above or below, the dispensing device comprises an ophthalmic liquid composition further comprising a surfactant. In a preferred embodiment the surfactant is a non-ionic surfactant, for their solubilizing effect and for preventing the adsorption of the prostaglandin analogues to the dispensing device. In a more preferred embodiment, the non-ionic surfactant is selected from the group consisting of polysorbate 80, polysorbate 60, polysorbate 40, poly(oxythylene)sorbitan monolaurate, poly(oxyethylene)sorbitan trioleate, polysorbate 65, polyoxyethylene hydrogenated castor oil 10, polyoxyethylene hydrogenated castor oil 50, polyoxyethylene hydrogenated castor oil 60, polyoxyethylene hydrogenated castor oil 40, polyoxyl 40 stearate and mixtures thereof. The non-ionic surfactants can be used individually or in combination. In an even more preferred embodiment, the non-ionic surfactant is polysorbate 80 or polyoxyethylene hydrogenated castor oil 40.

The term "antioxidant" refers to a compound that prevents the oxidation of other molecules. Examples of suitable antioxidant include ethylenediamine tetraacetic acid (also known as edetic acid) and salts thereof (for example, disodium edetate), dibutyl hydroxy toluene and the like.

The term "tonicity agent" refers to a compound designed to reduce local irritation by preventing osmotic shock at the site of application. Examples of the tonicity agent include sodium chloride, potassium chloride, calcium chloride, propylene glycol, glycerol, sorbitol, mannitol and the like.

The term "buffering agent" refers to a substance capable in solution of neutralizing both acids and bases and thereby maintaining the original acidity or basicity of the solution. Specific examples of buffers include but are not limited to boric acid, borax, citric acid, disodium hydrogenphosphate, ε-aminocaproic acid and the like.

As is well known to the skilled in the art, a buffering agent is a system generally consisting of an acid and its conjugate base. The preparation of buffering agents is also well known, thus, for example, the phosphate buffer is typically prepared as a mixture of the dihydrogen phosphate ion and the hydrogen phosphate ion, for example using the sodium dihydrogen phosphate salt ($NaH_2PO_4$, or monosodium phosphate) preferably sodium dihydrogen phosphate monohydrate ($NaH_2PO_4 \cdot H_2O$), and the sodium hydrogen phosphate salt ($Na_2HPO_4$, or disodium phosphate). Analogously, the acetate buffer can be prepared with acetic acid and sodium acetate; the citrate buffer can be prepared with citric acid and sodium citrate; or the borate buffer can be prepared with boric acid and disodium tetraborate, for example.

The method for preparing the eye drop containing the present prostaglandin analogue can be any conventional method for preparation without need of special procedure or operation. The pH of the eye drop solution according to the invention is preferably adjusted to a value of from 3 to 8, particularly from 4 to 7. As pH adjusting agents, common pH agents such as sodium hydroxide and/or hydrochloric acid may be used.

In another embodiment of the present invention, optionally in combination with one or more features of the various embodiments described above or below, the dispensing device preferably comprises a preservative-free ophthalmic liquid composition.

Within this description, the "preservative-free ophthalmic solution" means that the ophthalmic solution of the present invention does not comprise a preservative, such as quaternary ammonium salts, e.g. benzalkonium chloride (BAC). Other pharmaceutically acceptable preservatives for ophthalmic solutions are for example boric acid-polyol-zinc chloride or chlorine oxide compounds, chlorhexidine gluconate, benzethonium chloride, sorbic acid, potassium sorbate, ethyl p-hydroxybenzoate and butyl p-hydroxybenzoate.

The skilled person will appreciate that any substance that is known to provide a preservative effect should be excluded in this context, irrespective of any other function that the substance could simultaneously have in the liquid preparation.

Preservatives are commonly added in order to guarantee the sterility of the solution after first opening of the device. However, these preservatives, which could contribute to the solubilization of the active ingredient and its stabilization within the solution, are now deprecated because they can be toxic and pose problems of tolerance, especially in the context of a long-term treatment such as glaucoma. Therefore, a preservative-free liquid composition is preferred in the present invention. The solubilization of the active ingredient and its stability in the device is therefore likely to be affected.

In an embodiment, the ophthalmic liquid composition contained within the dispensing device of the invention is an aqueous solution comprising latanoprost as active ingredient, the non-ionic surfactant polysorbate 80, disodium edetate as antioxidant, a tonicity agent, and a buffering agent.

In a preferred embodiment, said ophthalmic liquid composition is an aqueous solution comprising:

latanoprost in a concentration comprised in the range 0.010-0.100 mg/ml, preferably in the range 0.020-0.080 mg/ml, more preferably in the range 0.030-0.070 mg/ml, still more preferably in the range 0.040-0.060 mg/ml, still more preferably in a concentration of about 0.050 mg/ml and still more preferably in a concentration of 0.050 mg/ml;

polysorbate 80 in a concentration comprised in the range 0.1-10.0 mg/ml, preferably in the range 0.1-5.0 mg/ml, more preferably in the range 0.2-1.0 mg/ml, still more preferably in the range 0.30-0.70 mg/ml, still more preferably in the range 0.40-0.60 mg/ml, still more preferably is about 0.50 mg/ml, and still more preferably is 0.50 mg/ml;

disodium edetate in a concentration comprised in the range 0.1-0.5 mg/ml, preferably in the range 0.1-0.4 mg/ml, more preferably is about 0.2 mg/ml, and still more preferably is 0.2 mg/ml;

a tonicity agent in an amount sufficient to adjust the osmolality to a value comprised in the range 250-320 mOsmol/kg, preferably wherein the tonicity agent is selected from the group consisting of sodium chloride, potassium chloride, calcium chloride, propylene glycol, glycerol, sorbitol, mannitol and mixtures thereof, and more preferably the tonicity agent is sodium chloride; and an ophthalmically-acceptable buffering agent, preferably selected from acetate, citrate, phosphate, and borate buffers, more preferably is a phosphate buffer;

optionally, a pH adjusting agent such as hydrochloric acid and/or sodium hydroxide to adjust the pH of the solution to a value in the range 5.5-6.5, preferably in the range 5.8-6.2, more preferably to about 6.0; and water, as solvent;

wherein, more preferably, the tonicity agent is sodium chloride in an amount comprised in the range 1.0-9.0 mg/ml; preferably in the range 4.0-6.0 mg/ml; more preferably in the range 4.0-5.0 mg/ml, and still more preferably is about 4.6 mg/ml.

It is understood that said aqueous composition has a pH value in the range 5.5-6.5, preferably in the range 5.8-6.2, more preferably about 6.0, and still more preferably the pH is 6.0. The use of the stated buffering agents may be sufficient to achieve the desired pH value, or it may be necessary to add an additional pH adjusting agent, typically and acid and/or a base such as hydrochloric acid and/or sodium hydroxide, to adjust the pH to the desired value.

Preferably, said the composition is preservative-free. In an embodiment, the ophthalmic composition contained within the dispensing device of the invention is an aqueous solution which essentially consists of latanoprost, polysorbate 80, sodium edetate, a tonicity agent, a buffering system, optionally a pH adjusting agent, and water as solvent, according to the preferences disclosed above.

In a further embodiment of the present invention, optionally in combination with one or more features of the various embodiments described above or below, the dispensing device comprises an ophthalmic liquid composition comprising a prostaglandin analogue in combination with at least one further pharmaceutically active substance, preferably a β-blocking agent, more preferably timolol, or a pharmaceutically acceptable salt thereof. In a preferred embodiment, the ophthalmic liquid composition comprises the combination of latanoprost and timolol, or a pharmaceutically acceptable salt thereof, as active ingredients. A preferred pharmaceutically acceptable salt of timolol is timolol maleate.

In an embodiment, the ophthalmic liquid composition contained within the dispensing device of the invention is an aqueous solution comprising latanoprost and timolol, or a pharmaceutically acceptable salt thereof, as active ingredients, the non-ionic surfactant polysorbate 80, disodium edetate as antioxidant, a tonicity agent, and a buffering agent.

In a preferred embodiment, said ophthalmic liquid composition is an aqueous solution comprising:

latanoprost in a concentration comprised in the range 0.010-0.100 mg/ml, preferably in the range 0.020-0.080 mg/ml, more preferably in the range 0.030-0.070 mg/ml, still more preferably in the range 0.040-0.060 mg/ml, still more preferably in a concentration of about 0.050 mg/ml and still more preferably in a concentration of 0.050 mg/ml;

timolol, or a pharmaceutically acceptable salt thereof, preferably timolol maleate, in a concentration comprised in the range 1-10 mg/ml, preferably in the range 2-8 mg/ml, more preferably in the range 3-7 mg/ml, still more preferably in the range 4-6 mg/ml, still more preferably in a concentration of about 5.0 mg/ml and still more preferably in a concentration of 5.0 mg/ml;

polysorbate 80 in a concentration comprised in the range 0.1-10.0 mg/ml, preferably in the range 0.1-5.0 mg/ml, more preferably in the range 0.2-1.0 mg/ml, still more preferably in the range 0.30-0.70 mg/ml, still more preferably in the range 0.40-0.60 mg/ml, still more preferably is about 0.50 mg/ml, and still more preferably is 0.50 mg/ml;

disodium edetate in a concentration comprised in the range 0.1-0.5 mg/ml; preferably in the range 0.1-0.4 mg/ml; more preferably is about 0.2 mg/ml, and still more preferably is 0.2 mg/ml;

a tonicity agent in an amount sufficient to adjust the osmolality to a value comprised in the range 250-320 mOsmol/kg, preferably wherein the tonicity agent is selected from the group consisting of sodium chloride, potassium chloride, calcium chloride, propylene glycol, glycerol, sorbitol, mannitol and mixtures thereof, and more preferably the tonicity agent is sodium chloride;

an ophthalmically-acceptable buffering agent, preferably selected from acetate, citrate, phosphate, and borate buffers, more preferably is a phosphate buffer;

optionally, a pH adjusting agent such as hydrochloric acid and/or sodium hydroxide to adjust the pH of the solution to a value in the range 5.5-6.5, preferably in the range 5.8-6.2, more preferably to about 6.0; and water, as solvent.

When timolol is used as a pharmaceutically acceptable salt thereof, the stated preferred concentrations refer to the equivalent amount of timolol.

Preferably, the composition is preservative-free. In an embodiment, the ophthalmic composition contained within the dispensing device of the invention is an aqueous solution which essentially consists of latanoprost, timolol or a pharmaceutically acceptable salt thereof, polysorbate 80, sodium edetate, a tonicity agent, a buffering system, optionally a pH adjusting agent, and water as solvent, in the preferred embodiments and amounts as disclosed above.

As shown in the examples, namely, in stability tests 3 and 4, the latanoprost aqueous ophthalmic solutions prepared, containing very low concentration of surfactant (polysorbate 80) and antioxidant (disodium edetate), and which are preservative-free, surprisingly, not only are very stable in terms of the amount of latanoprost, but also the amount of impurities is remarkably low (see tables 2 and 3). Therefore, another aspect of the invention is a preservative-free aqueous ophthalmic solution comprising:

- latanoprost in a concentration comprised in the range 0.010-0.100 mg/ml, preferably in the range 0.020-0.080 mg/ml, more preferably in the range 0.030-0.070 mg/ml, still more preferably in the range 0.040-0.060 mg/ml, still more preferably in a concentration of about 0.050 mg/ml and still more preferably in a concentration of 0.050 mg/ml;
- optionally, timolol or a pharmaceutically acceptable salt thereof, preferably timolol maleate, in a concentration comprised in the range 1-10 mg/ml, preferably in the range 2-8 mg/ml, more preferably in the range 3-7 mg/ml, still more preferably in the range 4-6 mg/ml, still more preferably in a concentration of about 5.0 mg/ml and still more preferably in a concentration of 5.0 mg/ml;
- polysorbate 80 in a concentration comprised in the range 0.1-10.0 mg/ml, preferably in the range 0.1-5.0 mg/ml, more preferably in the range 0.2-1.0 mg/ml, still more preferably in the range 0.30-0.70 mg/ml, still more preferably in the range 0.40-0.60 mg/ml, still more preferably is about 0.50 mg/ml, and still more preferably is 0.50 mg/ml;
- disodium edetate in a concentration comprised in the range 0.1-0.5 mg/ml, preferably in the range 0.1-0.4 mg/ml, more preferably is about 0.2 mg/ml, and still more preferably is 0.2 mg/ml;
- a tonicity agent in an amount sufficient to adjust the osmolality to a value comprised in the range 250-320 mOsmol/kg, preferably wherein the tonicity agent is selected from the group consisting of sodium chloride, potassium chloride, calcium chloride, propylene glycol, glycerol, sorbitol, mannitol and mixtures thereof, and more preferably the tonicity agent is sodium chloride;
- an ophthalmically-acceptable buffering agent, preferably selected from acetate, citrate, phosphate, and borate buffers, more preferably is a phosphate buffer;
- optionally, a pH adjusting agent such as hydrochloric acid and/or sodium hydroxide to adjust the pH of the solution to a value in the range 5.5-6.5, preferably in the range 5.8-6.2, more preferably to about 6.0; and
- water, as solvent.

Preferably, said ophthalmic composition essentially consists of the stated ingredients, i.e., latanoprost, optionally timolol or a pharmaceutically acceptable salt thereof, polysorbate 80, disodium edetate, a tonicity agent, the buffering agent, optionally a pH adjusting agent, and water.

Plasticisers are additives that increase the plasticity or decrease the viscosity of a polymer. Example of plasticisers are ethylene-vinyl acetate (EVA, a copolymer of ethylene and vinyl acetate), a rubber-like materials, such as butyl rubber.

Plasticisers also called softeners because they also provide softness which helps to ensure the required tightness of the packaging.

In a further embodiment of the present invention, optionally in combination with one or more features of the various embodiments described above or below, the dispensing device comprises a container with an ophthalmic liquid composition comprising a prostaglandin analogue packaged therein, a dropper and a gasket, wherein said gasket is made of a polymer selected from a group consisting of polyethylene, polypropylene, polytetrafluoroethylene and mixtures thereof. In a preferred embodiment the polymer of the gasket is polyethylene.

Dispensing device with a gasket made of polyethylene substantially free of plasticiser meets the tightness requirements according to USP NF. Water loss is 0.74% as calculated for 365 days at 25° C./40 RH.

Moreover, product in the dispensing device of the present invention meets the water loss requirements defined in the EMA guideline; *Stability Testing of New Drug Substances and Products*.

A container is referred herein also as a bottle, reservoir or vessel.

In an embodiment of the present invention, optionally in combination with one or more features of the various embodiments described above or below, the dispensing device comprises an ophthalmic liquid composition comprising a prostaglandin analogue packaged in a container made of a polymer selected from a group consisting of polyethylene (PE), polypropylene (PP), polyethylene terephthalate (PET), polyvinyl chloride, acrylic resins, polystyrene, polymethylmethacrylate, nylon 6 and mixtures thereof. In a preferred embodiment, the container is made of a polymer selected from a group consisting of polyethylene (PE) and polypropylene (PP). These polymers can be high-density or low-density polymers, e.g. high density polyethylene (HDPE).

Containers made of PP as well as PE are shatterproof and lightweight. These materials are well known and used for decades. In relation to the extractables they are considered safe and neutral to the packaging content.

In a further embodiment of the present invention, optionally in combination with one or more features of the various embodiments described above or below, the gasket for the dispensing device as disclosed herein is made of a polymer selected from a group consisting of polyethylene, polypropylene, polytetrafluoroethylene and mixtures thereof. In a preferred embodiment the polymer is polyethylene.

EXAMPLES

The effect of the plasticiser on the adsorption of prostaglandin analogues to gaskets was studied for up to three months storage at 25° C./40% RH.

1. Preparation of Prostaglandin Analogues Compositions

| 1.1. Formulation 1 | |
|---|---|
| Substance | [mg/ml] |
| Latanoprost | 0.050 |
| Polysorbate 80 | 0.50 |
| Disodium edetate | 0.20 |

-continued

1.1. Formulation 1

| Substance | [mg/ml] |
|---|---|
| Sodium chloride | 4.61 |
| Disodium phosphate | 1.6 |
| Sodium dihydrogen phosphate monohydrate | 7.7 |
| Sodium hydroxide solution | q.s. to pH 6.0 |
| Hydrochloric acid, dilute | q.s. to pH 6.0 |
| Water for injections | Up to 1 ml |

1.2. Formulation 2

| Substance | [mg/ml] |
|---|---|
| Travoprost | 0.04 |
| Sodium chloride | 3.5 |
| Boric acid | 3.0 |
| Polyoxyethylene (40) Hydrogenated Castor Oil | 2.0-5.0 |
| Propylene glycol | 7.5 |
| Mannitol | 3.0 |
| 1M sodium hydroxide/ 1M Hydrochloric acid | q.s. up to pH 4.6-6.8 |
| Water for injection | Up to 1 ml |

1.3. Formulation 3

| Substance | [mg/ml] |
|---|---|
| Tafluprost | 0.015 mg |
| Glycerol | 22.5 mg |
| Sodium dihydrogen phosphate dihydrate | 2.0 mg |
| Disodium edetate | 0.5 mg |
| Polysorbate 80 | 0.75 mg |
| Highly purified water | up to 1.0 ml |

1.4. Formulation 4

| Substance | [mg/ml] |
|---|---|
| Latanoprost | 0.05 |
| Timolol maleate | 6.83 |
| Sodium chloride | 4.3 |
| Polysorbate 80 | 0.5 |
| Disodium edetate | 0.2 |
| Disodium phosphate | 2.6 |
| Sodium dihydrogen phosphate monohydrate | 6.2 |
| Hydrochloric acid, dilute | q.s. up to pH 5.5-6.5 |
| Sodium hydroxide/1M | q.s. up to pH 5.5-7.5 |
| Water, highly purified | Up to 1 mL |

2. Manufacture of the Container

The bottles were obtained through fabrication by injection blow moulding of polypropylene (PP) or polyethylene (PE). All the bottles are containers for eye drops having the same shape.

3. Manufacture of the Dropper

The closure system consists of a pump system applied on the snap-on bottle.

The gasket made of PE/EVA comprises 30% Evatane® 28-05, which is less than 10% of ethylene-vinyl acetate (EVA).

The gasket made of PE without EVA is 100% PE.

Before the device is filled with the ophthalmic solution, the container and the dropper are sterilized by any convenient method including, without limitation, ethylene oxide, autoclaving, irradiation, and the like or combination thereof. Preferably, sterilization is carried out using gamma radiation or using ethylene oxide.

4. Test Method

After storage at different conditions for up to three months, the content of the prostaglandin analogue in each bottle was determined by a high performance liquid chromatography (HPLC), similarly to the amount of impurities in results of Stability tests 3 and 4.

HPLC method with diode array detection (DAD) was used. Analyses were performed by means analytical columns with L40 stationary phase (according to USP) or using a set of two analytical columns joined by a connector: one with L40 stationary phase and a second column filled with L10 stationary phase (designations L40 and L10 according to USP).

As mobile phase, a mixture of phase A (acetonitrile, water and phosphoric acid 85%) and phase B (acetonitrile) was used, administered as a gradient elution.

The dispensing device was stored in inverted position, in order to assure the full contact of the solution with the gasket.

A loss of the prostaglandin analogue present in the preparation refers to the difference (%) between the concentration of prostaglandin analogue existing in the liquid preparation after a predetermined period of time, and the original concentration of prostaglandin analogue present in the preparation.

4.1. Stability Test 1

The obtained results after storage at 25° C./40% RH are shown in Table 1.

TABLE 1

| | | Conc. (%) | | |
|---|---|---|---|---|
| | | Day 0 | 1 month | % loss |
| Comparative Example 1 | Formulation 1 HDPE container Dropper with PE/EVA gasket | 99.6 | 95.5 | 4.1 |
| Example 1 | Formulation 1 HDPE container Dropper with PE gasket | 100.0 | 98.7 | 1.3 |
| Example 2 | Formulation 1 PP container Dropper with PE gasket | 100.0 | 97.6 | 2.4 |
| Example 3 | Formulation 1 HDPE container Dropper without gasket | 100.1 | 99.7 | 0.4 |

The concentration of latanoprost in the table means the percentage of latanoprost in relation to the declared content (50 µg/ml).

Results in Table 1 show that the concentration of the active ingredient of the Formulation 1 (latanoprost) in the Examples 1 and 2 is higher than the concentration in the Comparative Example 1, and the product loss in the aqueous solution is reduced at Examples 1 and 2. Adsorption of the present compound to the ophthalmic dispenser was remarkably inhibited.

The results obtained for Example 3 showed that the gasket material was responsible for the adsorption of the active ingredient in the dispensing device. However, the gasket was needed in order to provide the required tightness to the packaging.

4.2. Stability Test 2

The obtained results after storage at temperature between 2-8° C. are shown in Table 3.

TABLE 2

|  |  | Conc. (%) | | |
| --- | --- | --- | --- | --- |
|  |  | Day 0 | 1 month | % loss |
| Comparative Example 2 | Formulation 1 HDPE container Dropper with PE/EVA gasket | 99.6 | 97.1 | 2.6 |
| Example 4 | Formulation 1 HDPE container Dropper with PE gasket | 100.0 | 99.0 | 1.0 |
| Example 5 | Formulation 1 PP container Dropper with PE gasket | 100.0 | 99.1 | 0.9 |

As it is shown in Table 2, at lower temperature, the adsorption of the active ingredient to the dispenser decreased for all the Examples.

It has been also found that the concentration of the active ingredient in the Formulation 1 (latanoprost) in the Examples 4 and 5 is higher than the concentration in the Comparative Example 2.

4.3. Stability Test 3

A composition of latanoprost (Formulation 1) in HDPE container with a dropper with PE gasket was subjected to 9-month stability study at 25±2° C./60±5% RH, wherein not only the concentration of the active ingredient (latanoprost), but also the content of the main impurities were determined by HPLC.

The concentration of latanoprost means the percentage of latanoprost in relation to the declared content (50 µg/ml). The concentration of impurities means the amount of impurities, expressed as % (w/v).

Results are shown in Table 3.

TABLE 3

|  | Month | | | | | |
| --- | --- | --- | --- | --- | --- | --- |
|  | 0 | 1 | 3 | 5 | 6 | 9 |
| Latanoprost | 100.0 | 98.7 | 101.3 | 101.2 | 100.1 | 99.2 |
| Impurity A | <LOD | <LOD | <LOD | <LOD | <LOD | <LOD |
| Impurity B | <LOD | <LOD | <LOD | <LOD | <LOD | <LOD |
| Impurity E | 0.1 | 0.12 | 0.35 | 0.31 | 0.34 | 0.36 |
| Any other single impurity | <LOD | <LOD | <LOD | <LOD | <LOD | <LOD |
| Sum of impurities excluding impurities A, B, E | <LOD | <LOD | <LOD | <LOD | <LOD | <LOD |

(LOD in the table means "limit of detection" of the method)

It was surprisingly found that, not only the content of the active ingredient was very stable, but the level of impurities was very low, despite the fact that the composition does not contain any preservative.

4.4. Stability Test 4

A comparative stability test was performed comparing three batches of a composition and dispensing device according to the invention (latanoprost ophthalmic composition of Formulation 1 in HDPE container with a dropper with PE gasket) (Batches 1-A, 1-B and 1-C) vs. three batches of reference latanoprost ophthalmic composition (Ref-A, Ref-B and Ref-C), comprising benzalkonium chloride (BAC) as preservative and stored in a dropper container of PE with a screw cap and tamper evident overcap of PE.

The reference Xalatan® is an aqueous formulation comprising 0.05 mg/ml of latanoprost and 0.2 mg/ml of BAC as preservative.

Both the compositions according to the invention and the reference compositions were subjected to stability at 25±2° C./60±5% RH. The concentration of latanoprost, impurity E and of the sum of impurities excluding impurities A, B and, E were determined by HPLC after 9 and 12 months of storage. The results are shown in Table 4.

TABLE 4

|  | Latanoprost | | Impurity E | | Sum of impurities | |
| --- | --- | --- | --- | --- | --- | --- |
|  | 9 m | 12 m | 9 m | 12 m | 9 m | 12 m |
| Batch-1A | 96.4 | 96.7 | 0.49 | 0.60 | <LOQ | <RT |
| Batch-1B | 98.9 | 98.9 | 0.45 | 0.54 | <RT | <RT |
| Batch-1C | 97.8 | 96.2 | 0.43 | 0.52 | 0.1 | 0.12 |
| Ref-A (expiry date October 2018) | 91.8 (analysed Jul. 8, 2017) | 93.0 (analysed Oct. 11, 2017) | 0.42 (analysed Jul. 8, 2017) | 0.59 (analysed Oct. 11, 2017) | 2.00 (analysed Jul. 8, 2017) | 2.80 (analysed Oct. 11, 2017) |
| Ref-B (expiry date November 2019) | 95.8 (analysed Aug. 9, 2018) | n.d. | 0.46 (analysed Aug. 9, 2018) | n.d. | 4.16 (analysed Aug. 9, 2018) | n.d. |
| Ref-C (expiry date September 2019) | n.d. | 93.8 (analysed Aug. 9, 2018) | n.d. | 0.56 (analysed Aug. 9, 2018) | n.d. | 4.98 (analysed Aug. 9, 2018) |

(LOQ in the table means "limit of quantification" of the method; RT means "retention threshold"; n.d. means "no data available")

It was surprisingly found that, compared to the reference composition comprising BAC as preservative, the composition according to the present invention (batches 1A, 1B and 10), which was preservative-free, was more stable, so the content of the active ingredient was higher than in the reference composition, the amount of impurity E was similar, while the amount of other impurities was lower, despite the fact that the composition of the invention does not contain any preservative.

4.5. Stability Test 5

The results obtained after storage at 25° C./40% RH are shown in Table 5.

TABLE 5

| | | Conc. (%) | | % loss |
|---|---|---|---|---|
| | | Day 0 | 3 months | after 3 months of storage |
| Comparative Example 3 | Formulation 2 HDPE container Dropper with PE/EVA gasket | 103.1 | 100.3 | 2.8 |
| Example 6 | Formulation 2 HDPE container Dropper with PE gasket | 100.6 | 100.6 | 0.0 |

Table 5 shows that there was no loss of the active ingredient of the Formulation 2 (travoprost) in the Example 6.

4.6. Stability Test 6

The obtained results after storage at 25° C./40% RH are shown in Table 6.

TABLE 6

| | | Conc. (%) | | | % loss after 3 months of storage |
|---|---|---|---|---|---|
| | | Day 0 | 1 month | 3 months | |
| Comparative Example 4 | Formulation 3 HDPE container Dropper with PE/EVA gasket | 98.4 | 94.5 | 90.0 | 8.4 |
| Example 7 | Formulation 3 HDPE container Dropper with PE gasket | 99.7 | 99.7 | 98.0 | 1.7 |

Results presented in Table 6 show that the concentration of the active ingredient (tafluprost) of the Formulation 3 in the Example 7 is higher than the concentration of the active ingredient of the Formulation 3 in the Comparative Example 4, and the loss of active ingredient in the aqueous solution is much lower in the Example 7. Adsorption of the active ingredient to the ophthalmic dispenser was remarkably inhibited.

4.7. Stability Test 7

The obtained results after storage at 25° C./40% RH are shown in Table 7.

TABLE 7

| | | Conc. (%) | | |
|---|---|---|---|---|
| | | Day 0 | 3 months | % loss |
| Example 8 | Formulation 4 HDPE container Dropper with PE gasket | 100.9 | 100.8 | 0.1 |

As it is shown at Table 7, the % loss of the active ingredient of Formulation 4 (tafluprost) in the Example 8 is very low and thus the adsorption of active ingredient is minimal.

5. Tightness Test for Dispensing Device 12 dispensing devices were selected and the tare weight was recorded.

10 Test containers were filled with water up to the fill capacity. Two containers were filled with glass beads, to the same weight as the filled test containers. The sealed containers were stored at a temperature of 25±2° and a relative humidity of 40±2%. After 336±1 h (14 days), the weight of the individual containers was recorded, and the water weight loss rate was calculated, in percent per year, for each bottle:

$$[(W_{1i}-W_T)-(W_{14i}-W_T)-(W_{C1}-W_{C14})] \times 365 \times 100 / (W_{1i}-W_T) \times 14$$

$W_{1i}$=initial weight of each individual bottle (i)

$W_T$=tare weight $W_{14i}$=weight of each individual bottle (i) at 14 days $W_{C1}$=initial weight of the control container at day 1

$W_{C14}$=weight of the control container at 14 days

Classification: the dispensing device meets the requirements for tight if the percentage of water weight loss does not exceed 2.5% per year in NMT 1 of the 10 test containers and does not exceed 5.0% per year in any of them.

For the dispensing device of the present invention, water loss of 0.74% as calculation for 365 days at 25° C./40 RH was determined.

6. Stability Testing

After 3 months of storage at accelerated conditions, 40° C./NMT 25% RH of the Formulation 1, the water loss in the dispensing device of the present invention did not exceed 5%, which according to a mentioned guideline is considered a significant change.

Results are presented in the Table 7 below:

TABLE 7

| Water loss after 3 months of storage at 40° C./NMT 25% RH | | | | | |
|---|---|---|---|---|---|
| Batch 1 | Batch 2 | Batch 3 | Batch 4 | Batch 5 | Batch 6 |
| 3.1% | 1.29% | 3.2% | 1.09% | 3.31% | 1.07% |

The results above confirm that the dispensing device of the present invention meets the tightness requirements, as defined by water loss in the EMA guideline *Stability Testing of New Drug Substances and Products*.

The invention claimed is:

1. A dispensing device comprising:
   an ophthalmic liquid composition comprising a prostaglandin analogue;
   a container with the ophthalmic liquid composition comprising the prostaglandin analogue packaged therein;
   a dropper; and
   a gasket,
   wherein the gasket is substantially free of plasticizer and the gasket comprises a polymer selected from the group consisting of polyethylene, polypropylene, polytetrafluoroethylene and mixtures thereof.

2. The dispensing device according to claim 1 wherein the prostaglandin analogue is a prostaglandin F2α analogue.

3. The dispensing device according to claim 1, wherein the ophthalmic liquid composition comprises a prostaglandin analogue in a concentration up to 100 micrograms/millilitre.

4. The dispensing device according to claim 1, wherein the ophthalmic liquid composition is an aqueous solution, an emulsion or a suspension.

5. The dispensing device according to claim 1, wherein the ophthalmic liquid composition further comprises a surfactant.

6. The dispensing device according to claim 1, wherein the ophthalmic liquid composition is preservative-free.

7. The dispensing device according to claim 1, wherein the ophthalmic liquid composition comprises at least one further pharmaceutically active substance.

8. The dispensing device according to claim 1, wherein the polymer consists of polyethylene.

9. The dispensing device according to claim 1, wherein the container comprises a polymer selected from the group consisting of polyethylene (PE), polypropylene (PP), polyethylene terephthalate (PET), polyvinyl chloride, acrylic resins, polystyrene, polymethylmethacrylate, nylon 6 and mixtures thereof.

10. The dispensing device according to claim 1, wherein the ophthalmic liquid composition is an aqueous solution comprising:
    latanoprost in a concentration comprised in the range 0.010-0.100 mg/ml;
    polysorbate 80 in a concentration comprised in the range 0.2-1.0 mg/ml;
    disodium edetate in a concentration comprised in the range 0.1-0.5 mg/ml;
    a tonicity agent in an amount sufficient to adjust the osmolality to a value comprised in the range 250-320 mOsmol/kg;
    an ophthalmically acceptable buffering agent;
    optionally, a pH adjusting agent to adjust the pH to a value in the range 5.5-6.5; and
    water, as solvent.

11. The dispensing device according to claim 10, wherein the tonicity agent is selected from the group consisting of sodium chloride, potassium chloride, calcium chloride, propylene glycol, glycerol, sorbitol, mannitol and mixtures thereof.

12. The dispensing device according to claim 10, wherein the buffering agent is selected from acetate, citrate, phosphate, and borate buffers.

13. The dispensing device as defined according to claim 10, wherein the ophthalmic liquid composition comprises timolol, or a pharmaceutically acceptable salt thereof, as a second active ingredient.

14. A gasket for the dispensing device as defined in claim 1.

15. The gasket according to claim 14, wherein said polymer consists of polyethylene.

16. A dropper for the dispensing device according to claim 1, comprising the gasket as defined in claim 14.

17. A preservative-free aqueous ophthalmic solution comprising:
    latanoprost in a concentration comprised in the range 0.010-0.100 mg/ml;
    optionally, timolol or a pharmaceutically acceptable salt thereof, in a concentration comprised in the range 1-10 mg/ml;
    polysorbate 80 in a concentration comprised in the range 0.2-1.0 mg/ml;
    disodium edetate in a concentration comprised in the range 0.1-0.5 mg/ml;
    a tonicity agent in an amount sufficient to adjust the osmolality to a value comprised in the range 250-320 mOsmol/kg;
    an ophthalmically-acceptable buffering agent;
    optionally, a pH adjusting agent, to adjust the pH to a value in the range 5.5-6.5; and
    water, as solvent.

18. A dispensing device comprising:
    an ophthalmic liquid composition comprising a prostaglandin analogue;
    a container with the ophthalmic liquid composition comprising the prostaglandin analogue packaged therein;
    a dropper; and
    a gasket,
    wherein the gasket comprises 2% or less of plasticizer and the gasket comprises a polymer selected from the group consisting of polyethylene, polypropylene, polytetrafluoroethylene and mixtures thereof.

19. The dispensing device according to claim 18, wherein the gasket consists of polyethylene.

* * * * *